US009173640B2

(12) United States Patent
Lin

(10) Patent No.: US 9,173,640 B2
(45) Date of Patent: Nov. 3, 2015

(54) SYSTEMS AND METHODS FOR PROCESSING ULTRASOUND COLOR FLOW MAPPING

(71) Applicant: Shengtz Lin, Cupertino, CA (US)

(72) Inventor: Shengtz Lin, Cupertino, CA (US)

(73) Assignee: SONOWISE, INC., San Jose, CA (US)

( * ) Notice: Subject to any disclaimer, the term of this patent is extended or adjusted under 35 U.S.C. 154(b) by 179 days.

(21) Appl. No.: 13/963,509

(22) Filed: Aug. 9, 2013

(65) Prior Publication Data

US 2015/0045666 A1 Feb. 12, 2015

(51) Int. Cl.
*A61B 8/00* (2006.01)
*A61B 8/08* (2006.01)
*A61B 8/06* (2006.01)

(52) U.S. Cl.
CPC ............ *A61B 8/5223* (2013.01); *A61B 8/06* (2013.01); *A61B 8/461* (2013.01); *A61B 8/5207* (2013.01); *A61B 8/0891* (2013.01); *A61B 8/488* (2013.01)

(58) Field of Classification Search
CPC .......... A61B 8/06; A61B 8/463; A61B 8/488; A61B 8/5223; A61B 8/5246
See application file for complete search history.

(56) References Cited

U.S. PATENT DOCUMENTS

| | | |
|---|---|---|
| 5,482,044 A | 1/1996 | Lin et al. |
| 5,628,321 A | 5/1997 | Scheib et al. |
| 6,248,071 B1 | 6/2001 | Lin |
| 6,500,125 B1 | 12/2002 | Muzilla et al. |
| 6,520,915 B1 | 2/2003 | Lin et al. |
| 7,708,691 B2 | 5/2010 | Lin |
| 7,771,355 B2 | 8/2010 | Lin et al. |
| 8,016,758 B2 | 9/2011 | Wu |
| 8,287,455 B2 | 10/2012 | Phung |
| 8,317,707 B2 | 11/2012 | Lin et al. |
| 8,690,777 B2 | 4/2014 | Lin |
| 2009/0247874 A1 | 10/2009 | Kim |
| 2012/0029358 A1 | 2/2012 | Lin |
| 2013/0006115 A1 | 1/2013 | Phung |

OTHER PUBLICATIONS

Frank R. Kschischang, The Hilbert Transform, the Edward S. Rogers Sr. Department of Electrical and Computer Engineering, University of Toronto, Oct. 22, 2006, pp. 1-12.
Hans Torp, Signal processing in Ultrasound Doppler and Color Flow Imaging, Department of Circulation and Medical Imaging NTNU, Trondheim, Norway, pp. 1-22.

*Primary Examiner* — Jonathan Cwern
(74) *Attorney, Agent, or Firm* — K&L Gates LLP

(57) ABSTRACT

In one aspect, the invention relates to an ultrasound imaging system that includes an ultrasound receiver configured to receive ultrasound signals scattered from a sample in real time; an acoustic beam former; and an ultrasound data demodulation system. In one embodiment, the ultrasound imaging system further includes a processing system configured to process demodulated scan data and perform ultrasound image generation and flow processing and a display configured to show ultrasound image data and blood flow velocity data relative to such image data. Signals that include positive flow information and negative flow information are separated from received signals using phase-filters and analytic signal transforms such that a first and a second autocorrelation signal processing stage is used to generate mean positive flow, mean negative flow, and variance data for such flows.

13 Claims, 6 Drawing Sheets

Kidney Color Flow Image from Ultrasound Probe Scan and Signal Processing with Negative Flow (NF) and Positive Flow (PF) data

SYSTEMS AND METHODS FOR PROCESSING ULTRASOUND COLOR FLOW MAPPING

FIELD OF THE INVENTION

In general, the invention relates to the field of ultrasound color flow mapping. In particular, the invention relates to processing of ultrasound image data and detecting both positive and negative mean flow velocity parameters.

BACKGROUND OF THE INVENTION

Among the medical imaging modalities, ultrasound imaging technology is noninvasive, safe, affordable and generally easy to use. Ultrasound operates using a short burst mechanical wave transmitted into a patient's body. The echo reflected from structures in the patient's body is processed to form two dimensional or three-dimensional images for tissue and flow information. The frequency range for a noninvasive medical ultrasound imaging system is normally between 1 MHz to 15 MHz. The ultrasound images are normally displayed in realtime. Therefore, the operator or clinician can make an immediate diagnostic decision, or archive it for future comparison purposes.

As part of a given ultrasound data collection session, the data can be used to detect blood flow. Such flow detection can be performed using ultrasound Doppler imaging. A probe that includes one or more transducers can be used to transmit acoustic waves to and receive scattered waves from a sample of interest. The waves or echoes backscattered from the sample include information about the sample and its properties and components. When it comes to detecting blood flow in a sample, the backscattered acoustic waves can be compared to a frequency reference to determine if a Doppler frequency shift occurred. Such a frequency shift can occur in the backscattered waves as a result of moving backscattering elements from the sample such as blood cells within an artery.

Further, such a frequency shift, which can also correspond to a phase shift, when detected using the ultrasound system, can be correlated with the velocity of the blood flow in the sample. The blood velocity is calculated by measuring the phase shift. The change or shift in backscattered frequency increases when blood flows toward the transducer and decreases when blood flows away from the transducer.

Color flow images are produced by superimposing a color image of the velocity of moving material, such as blood, over a gray scale anatomical B-mode image. Typically, a color flow mode displays hundreds of adjacent sample volumes simultaneously, all laid over a B-mode image to represent each sample volume's velocity. When arteries are adjacent, regions of overlap in an image can be challenging to resolve and result in ambiguities relating to flow direction. A need therefore exists for methods to resolve such ambiguities and improve upon color flow mapping techniques. The embodiments of the invention address these needs and others.

SUMMARY OF THE INVENTION

In one aspect, the invention relates to systems and methods of detecting a positive blood flow velocity and a negative blood flow velocity using an ultrasound imaging system. In one embodiment, the invention relates to a method for detecting blood flow when two blood vessels that are adjacent to each other are scanned using an ultrasound probe. Thus, positive and negative blood flow can be resolved when scanned together even though the flows overlap from the perspective of an ultrasound imaging probe.

In one aspect, the invention relates to an ultrasound data processing system that further includes a quadrature demodulation system. The quadrature demodulation system uses a first Hilbert transform configured to operate on a real signal and transform such a signal into an analytic signal. In one embodiment, the first Hilbert transform is applied to one or more signals in the quadrature phase (Q) channel. In one embodiment, a zero degree all pass filter is applied to one or more signals in the in-phase (I) channel. In part, the invention further relates to using a second Hilbert transform (also referred to herein as a Hilbert filter) in conjunction with a summer suitable for adding or subtracting signals after signal processing and a quadrature mixer in an ultrasound system to separate a positive flow signal and a negative flow signal for both the I and Q channels. In another aspect, the invention relates to the use of one or more Hilbert transform pairs as a signal processing stage to resolve overlapping flows as part of ultrasound color flow mapping. The second Hilbert transform output or subsets thereof can be used to perform autocorrelation processes to identify mean positive and negative flows.

In another aspect, the invention also relates to applying an autocorrelation process to the analytic signals resulting from the processing of the positive flow signals and the negative flow signals resulting from the application of one or more Hilbert transforms. In this way, the autocorrelation algorithm can be used to estimate mean signal values and variance signal values associated with positive directional flow and negative directional flow. This allows ambiguities relating to adjacent flow paths such as adjacent arteries to be resolved. In turn, the mean signal values and/or the variance signal values can be used to generate identifiers or indicia such as color which can then be used to perform color flow mapping mean positive and negative flows.

In one embodiment, the invention relates to resolving blood flowing in a positive direction relative to blood flowing in a negative direction in a sample volume such as within a kidney or a heart chamber. In one embodiment, resolution of adjacent blood flows is performed by selecting a pulse repetition frequency in the range of from about 1 KHz to about 50 KHz and using a transform, such as a Hilbert transform, to allow signals comprising flow data to be processed in the time domain, such as through an autocorrelation-based process, to reduce the number of data points that need to be acquired during scanning. In this way, signals that can contain flow data can be correlated with themselves to facilitate identifying relevant flow data. For a given color flow mapping, an embodiment of the invention determines the mean flow velocity in one or both directions and associated velocity variance values instead of a full spectrum of values for flow.

In one aspect, the invention relates to an ultrasound imaging system that includes an ultrasound receiver configured to receive ultrasound signals scattered from tissue or blood in real time; an acoustic beam former; and an ultrasound data demodulation system. In one embodiment, the ultrasound imaging system further includes a processing system configured to process demodulated scan data and perform ultrasound image generation and blood flow processing and a display configured to show ultrasound image data and blood flow velocity data relative to such image data. In one embodiment, the blood flow processing is implemented as a software module or a circuit or an application-specific integrated circuit configured to detect flow velocity or flow in either a positive or a negative flow direction.

In one embodiment, the detection of blood flow velocity is performed on a per color line signal basis. In one embodiment, a color line is a scan line in a specific beam direction extending from a point of a sound wave entering the body and echoing back towards the probe along the scan line in which different colors along such a scan line correspond to different parameters such as blood flows, turbulence, mean values, variance or other parameters. In one embodiment, the color flow mapping display is generated based on the processing of ultrasound data on a per color line signal basis, and form a two dimensional color flow image. In one embodiment, the blood flow velocity is a bi-flow velocity. In one embodiment, the bi-flow velocity is a mean velocity for either flow in the positive or negative direction based on acquired color line information. In one embodiment, bi-flow information with separate mean values can be encoded to have one color assigned for one direction (e.g. red for positive), and another color assigned for the other direction (e.g. blue for the negative), and another color (e.g. purple) assigned for the occurrence of combined flow in both positive and negative directions.

In one embodiment, the bi-flow mean or variance estimate is generated using an autocorrelation method after flow direction separation. The bi-flow mean or variance can be encoded using one or more indicia such as a color. In one embodiment, a color bar or another colored visual element can be used to display color flow information relative to ultrasound images generated following an ultrasound scan with a probe.

In one aspect, the invention relates to a method of ultrasound color flow mapping. The method includes separating a positive flow signal and a negative flow signal from ultrasound data using a first pair of Hilbert transforms; converting the separated positive flow signal and the separated negative flow signal into a positive flow analytic signal and a negative flow analytic signal using a second pair of Hilbert transforms; autocorrelating the positive flow analytic signal to obtain a mean positive flow velocity; autocorrelating the negative flow analytic signal to obtain a mean negative flow velocity; and performing color flow mapping using the mean positive flow velocity and the mean negative flow velocity. The method can further include determining a flow velocity variance using an autocorrelation process.

In one embodiment, performing color flow mapping further comprises using the flow velocity variance. The method of claim can further include collecting the ultrasound data using a probe. The method can further include selecting a data acquisition period during which the ultrasound data is collected by the probe that ranges from about 2 milliseconds to about 32 milliseconds. The method can further include the step of reducing occurrence of a spectral broadening artifact in response to the selection of the data acquisition period. The method can further include performing the autocorrelation steps using a time domain presentation of the positive flow analytic signal and the negative flow analytic signal.

The method can further include applying a first indicia to ultrasound image data corresponding to the mean positive flow; and applying a second indicia to ultrasound image data corresponding to the mean negative flow. The method can further include displaying ultrasound image data and the first indicia and the second indicia overlaid on a B-mode image. The method can further include assigning a first color code for the mean positive flow, assigning a second color code for the mean negative flow, and assigning a third color code for the flow with both positive and negative flow.

In one embodiment, the ultrasound data comprises one or more RF signals and can further include wall filtering the one or more RF signals to remove vessel wall motion; and frequency shifting the positive flow analytic signal and the negative flow analytic signal using a mixer. The method can further include selecting a pulse repetition frequency in the range of from about 1 KHz to about 50 KHz for the probe. In one embodiment, a phase angle for one Hilbert transform of the first pair is set at about 0 degrees and a phase angle for the other Hilbert transform of the first pair is set at about 90 degrees.

In one aspect, the invention relates to a method of ultrasound color flow mapping. The method includes transforming one or more RF signals received from an ultrasound probe into one or more analytic signals using a first Hilbert transform; frequency shifting the one or more analytic signals to relative to a baseband using a complex mixer; wall filtering the one or more frequency shifted analytic signals to remove vessel wall motion; separating a first flow signal from the one or more wall filtered signals such that a first flow signal results; transforming the first flow signal into an analytic first flow signal using a second Hilbert transform; autocorrelating the analytic first flow signal to obtain a mean first flow velocity; and performing color flow mapping using the mean first flow velocity. The method can further include separating a second flow signal from the one or more wall filtered signals; transforming the first second flow signal into an analytic second flow signal using a third Hilbert transform; autocorrelating the analytic second flow signal to obtain a mean second flow velocity; and performing color flow mapping using the mean second flow velocity.

In one aspect, the invention relates to an ultrasound system. The system can include a mixer comprising a mixer input to receive radiofrequency (RF) signals from an ultrasound probe and a mixer output; a first wall filter comprising a first wall filter output and a first wall filter input in electrical communication with the mixer output; a second wall filter comprising a second wall filter output and a second wall filter input in electrical communication with the mixer output; a first Hilbert filter configured to perform a first Hilbert transform on an in-phase signal received from the first wall filter such that a Hilbert transformed in-phase signal results; a second Hilbert filter configured to perform a second Hilbert transform on a quadrature phase signal received from the second wall filter such that a Hilbert transformed quadrature signal results; a first summer in electrical communication with one or more of the first and second Hilbert filters, the first summer configured to receive one or more of the Hilbert transformed in-phase signal and the Hilbert transformed quadrature signal, the first summer comprising a first summer input and a first summer output; a second summer in electrical communication with one or more of the first and second Hilbert filters, the second summer configured to receive one or more of the Hilbert transformed in-phase signal and the Hilbert transformed quadrature signal, the second summer comprising a second summer input and a second summer output; a first signal processing device comprising a first analytic signal transform in electrical communication with the first summer output; and a second signal processing device comprising a second analytic signal transform in electrical communication with the second summer output; and a processing unit configured to perform autocorrelation on analytic signals received from the first and second signal processing devices.

In one embodiment, the first analytic signal transform is a first Hilbert transform having a first phase angle and a second Hilbert transform having a second phase angle. In one embodiment, the second analytic signal transform is a third Hilbert transform having a first phase angle and a fourth Hilbert transform having a second phase angle. The ultrasound system can further include a display, the display configured to receive color flow mode processing data from the processing unit, the processing unit configured to generate a positive mean flow and a negative mean flow in response to performing autocorrelation on the received analytic signals. In one embodiment, one or more of the Hilbert transforms are implemented using a device selected from the group consisting of a FPGA, a circuit, a filter, a finite impulse response (FIR), and an infinite impulse response (IIR) filter.

DETAILED DESCRIPTION

In part, embodiments of the invention relate to ultrasound systems and image and signal processing subsystems. In general, a probe that includes one or more transducers that generate acoustic waves for scanning a sample, such as a person, is used with various subsystems. The probe also receives echoes or backscattered waves from the sample. Blood moving within an artery or a vein results in a change in the backscattered waves or echoes received by the probe. These changes can be detected and evaluated along with image details of the sample being imaged using various techniques. Further, certain features relating to improvements regarding blood velocity resolution using Doppler techniques and image or pixel-based display features relating thereto are described below with regard to an embodiment of the invention.

A typical ultrasound imaging system includes a processor or other device configured to execute or implement algorithms for producing the 2D tissue Brightness mode (also called B-mode), tissue Motion mode (M-mode), spectra Doppler mode Pulsed Wave (PW) or Continuous Wave (CW), color flow mode (based on auto-correlation), and others. The B-mode image is displayed as the gray scale to represent the soft tissue of the internal organs being scanned. In one embodiment, the spectral Doppler uses fast Fourier transform (FFT) spectrum analysis to display the blood flow pattern in order to detect the degree of blood flow being blocked, such as by a stenosis, and other properties.

Figure 2:
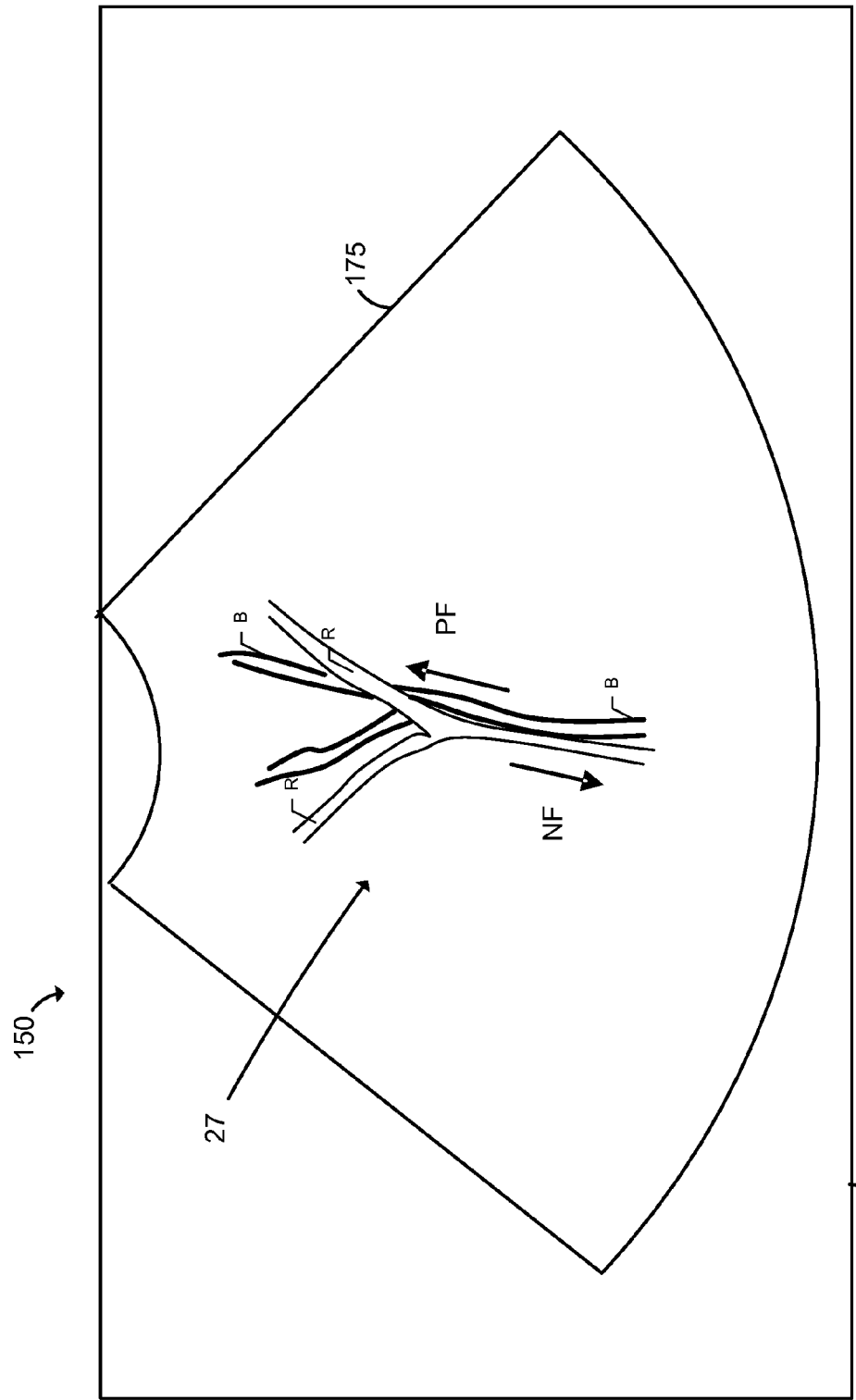
FIG. 2 is the color flow image with a color region of interest (CROI) displayed on top of a B-Mode image resulting from an ultrasound scan.
Figure 6:
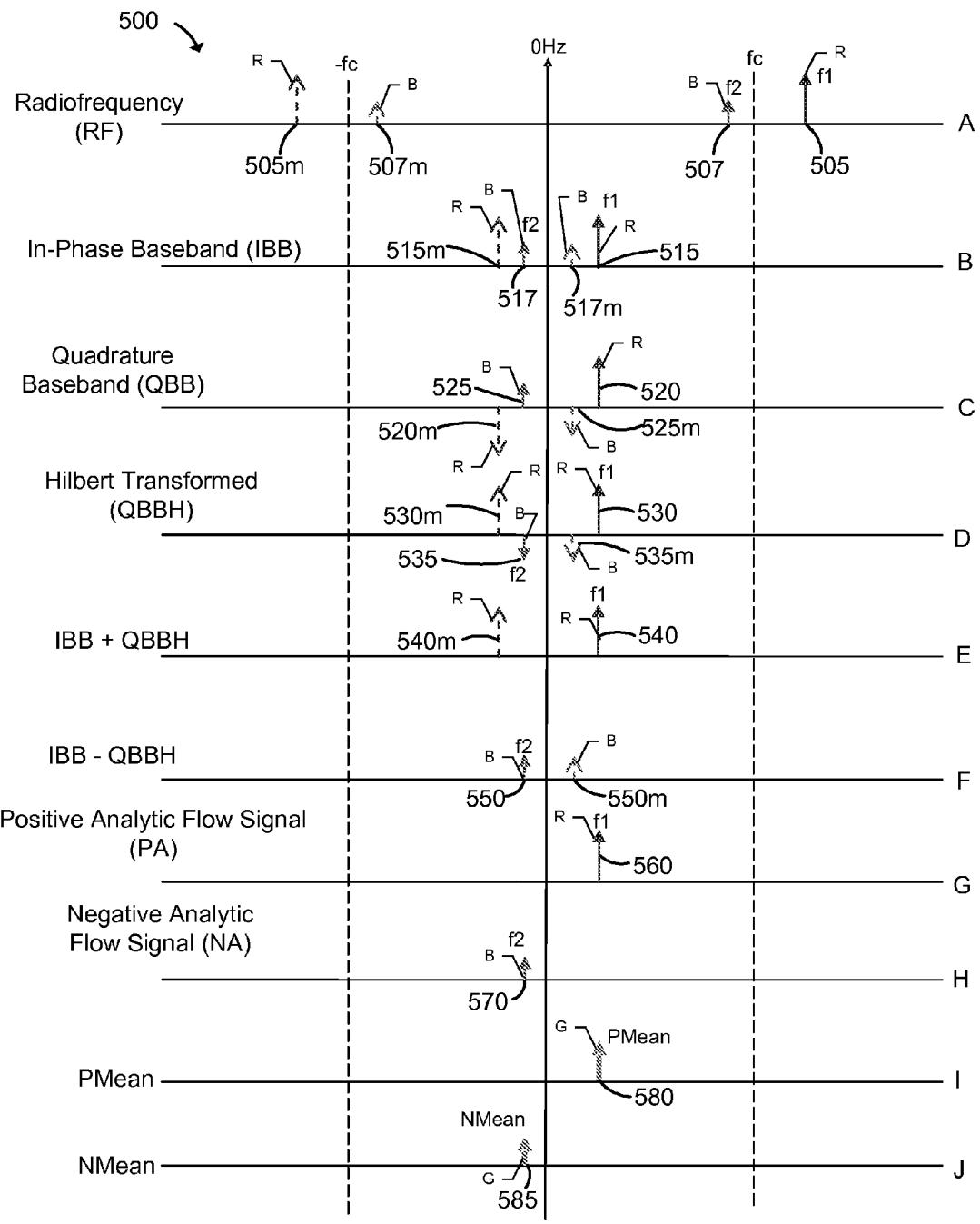
FIG. 6 is a series of spectrum representations A through J that include (from top to bottom radiofrequency (RF) signals, in-phase baseband (IBB) signals, quadrature baseband (QBB) signals, Hilbert transformed QBB signals (QBBH), the sum of the IBB signal and the QBBH signal, the difference of the IBB and the QBBH signal, the positive analytic flow signal (PA), the negative analytic flow signal (NA), a positive mean (PMean) flow signal, and a negative mean (NMean) flow signal in which the colors red (R), blue (B) and green (G) are used as indicia according to an embodiment of the invention.

In the case of Doppler imaging as part of color flow mode, the time varying phase signal P(t) is of interest because blood flow velocity in a target area is proportional to first derivative of P(t) with regard to time. The color flow mode is a two dimensional flow mapping that shows the blood flow in color and overlaid on top of the B-mode image (as shown in FIG. 2). Various indicia such as colors or hatching or symbols or other indicia can be used to overlay the flow mapping relative to the image data from the ultrasonic scan. PMean or positive mean flow and NMean or negative mean flow values can be mapped to the relevant indicia in one embodiment The pixels of the flow image can be color-coded as an implementation of color-based indicia. For example, pixels of one color, such as red pixels, can be used to represent the flow toward the ultrasound transducer of an imaging probe, and pixels of a second color, such as blue pixels, can be used to indicate flow away from the transducer. This color selection can be reversed or substituted with other color pairs without limitation. In some applications, the flow is shown by coding pixels with a third color such as a green color or other indicia to represent the turbulence. As discussed in more detail below, various signals can be represented as an image or in a frequency space as shown in FIG. 6 and described in more detail below.

In addition to color flow mode, the processing unit of the ultrasound system embodiments described herein can be configured to perform M-mode scans. M-mode is a real time motion modality suitable for displaying the heart muscle and valve movement in a cardiac ultrasound imaging application. Embodiments of the systems and method described herein, such as with regard to FIGS. 1 and 3, for example, can use one or more or combinations of the foregoing ultrasound modes and others.

Figure 1:
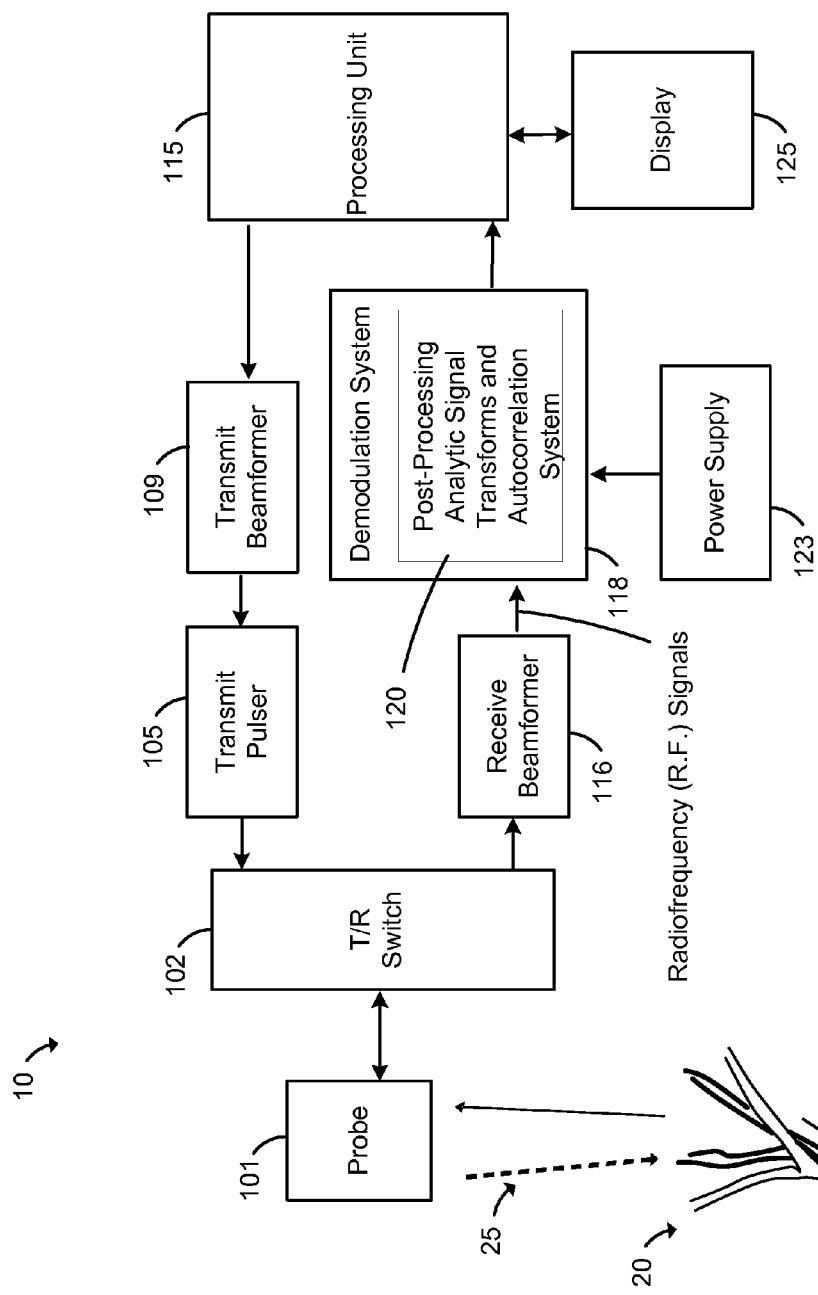
FIG. 1 is a block diagram of an ultrasound system configured to implement or include one or more color flow processing systems or related methods in accordance with an embodiment of the invention.

FIG. 1 shows an ultrasound system 10 suitable for implementing various embodiments of the invention relating to color flow mapping and other embodiments described herein. The system 10 can be used to scan a sample 20, such as a portion of a patient that includes one or more arteries, using sound waves 25. The system of FIG. 1 includes a probe 101 in electrical communication with a transmit and receive (T/R) switch 102. The probe sends and receives ultrasound waves 25 to and from the sample 20. A transmit pulser 105 is also in communication with the switch 102.

As shown in FIG. 1, the system 10 also includes a transmit beamformer 109 which is configured based on control signals from a processing unit 115 (also referred to herein as a processor). The processing unit or processor 115 can include one or more microprocessor or central processing units or computing devices. The processing unit can be configured to perform color flow mapping as outlined herein using signals transformed into analytic signals, FFT processes, and autocorrelation features described herein to generate positive mean flow data and negative mean flow data. A receive beamformer 116 receives RF signals returning from the probe 101 after being received by the switch 102. In one embodiment, the receive beamformer 116 is configured to sample the receive signals such as by Quadrature sampling. This sampling process transforms the received RF signals from the transducer in the probe such that a signal pair results the I (in-phase) and the Q (quadrature) signals. These can be referred to as the I and Q signal pair or the I/Q signal and in other forms as described below.

After passing the T/R switch, the RF signals routed to the receive beamformer 116 and sampled I/Q signal pairs are sent to a demodulation system 118 or other subsystems for signal processing. In part, the demodulation system 118 can be configured to remove the carrier frequency from the I/Q signal pairs. The demodulation system 118 can include a signal processing system such as a post-processing analytic signal transform and autocorrelation system 120. System 120 can also be separate from the demodulation system 118 or part of the processing unit 115. The system 120 can include circuits, processors or other electrical devices suitable for applying a transform to the I/Q signal pairs such as a Hilbert transform or other transform resulting in analytic signal generation. Further, the system 120 can also include circuits, processors or other electrical devices suitable for performing autocorrelation with regard to transformed ultrasound signals. A power supply 123 can be in electrical communication with the system 10, such as through the demodulation system 118.

The system 10 can also include a display and user interface 125. This can allow the user to specify color flow mapping properties relating to mean negative flow data and positive flow data resulting from autocorrelation and other signal processing performed by one or both of the demodulation system 118 or the processing unit 115.

With regard to displaying color flow mapping 150, display 125 can be used. As shown in FIG. 2, the region of interest in the sample 27 called color region of interest (CROI), is overlaid on top of the B-Mode image 175 to generate the color flow mode display 150 with use of red (R) and blue (B) color coding and/or the positive (PF) and negative flow (NF) direction arrows shown. Arterial and Venous flow are shown mixing together in the color flow mode image 150 of FIG. 2. The CROI is virtually divided into multiple sample volumes along a scan line. Each sample volume is interrogated by transmitting the ultrasound energy from a probe such as probe 101. The probe receives the echo from sample 20.

The ultrasound waves can be generated by the probe in various sequences such as by energizing transducers in the probe to generate a plurality of burst pulses. For example in the color flow mode, a given probe can generate between about 6 to about 12 pulses which impinge on the sample of interest 20, such as region of a body with one or more overlaid arties. For each pulse, a corresponding echo or backscattered wave is received such that a packet of ensemble data is generated for subsequent data processing and display. For example, the sample 20 is scanned using probe 101 and an ultrasound-based image of the sample 25 is displayed using a display such as display 125 of FIG. 1. The ultrasound image 25 shows arterial branches and veins through which blood flows in a kidney.

Color flow mapping is based on detecting the phase shift of the echo from each data point within the packet of that sample volume in the CROI. Therefore, each sample volume is interrogated multiple times in order to calculate the reliable phase difference of the blood movement. Further, the ultrasound waves returning from the body as a result of interrogation by the probe for each sample volume form an ensemble packet. As described herein, various methods steps are used to process such an ensemble packet, including various transforms, filters, and autocorrelation steps, to calculate blood velocity, mean positive flow data, mean negative flow data, and other parameters as described herein.

When the scanned blood vessels are small, and curving closely together at various directions within the color sample volume as in FIG. 2, the ultrasound interrogation cannot resolve the vessels in either the lateral dimension or in an elevation dimension. As a result, the positive flow (PF) and negative flow (NF) from the same sample volume are ambiguous. With legacy approaches, the user has no way of knowing whether there are two vessels in the opposite direction within the same color sample volume, or indeed if the scanned volume of a sample has no blood flow at all because the mean flow estimate may give zero velocity. This problem is especially pronounced when imaging the kidney or blood flow relative to the heart. The methods and features described herein relating to signal processing and other features overcome these issues in legacy approaches. Additional details relating to the color flow-related embodiments of the invention can be explained using the system 10 of FIG. 1 and ultrasound subsystem 205 shown in FIG. 3.

Figure 3:
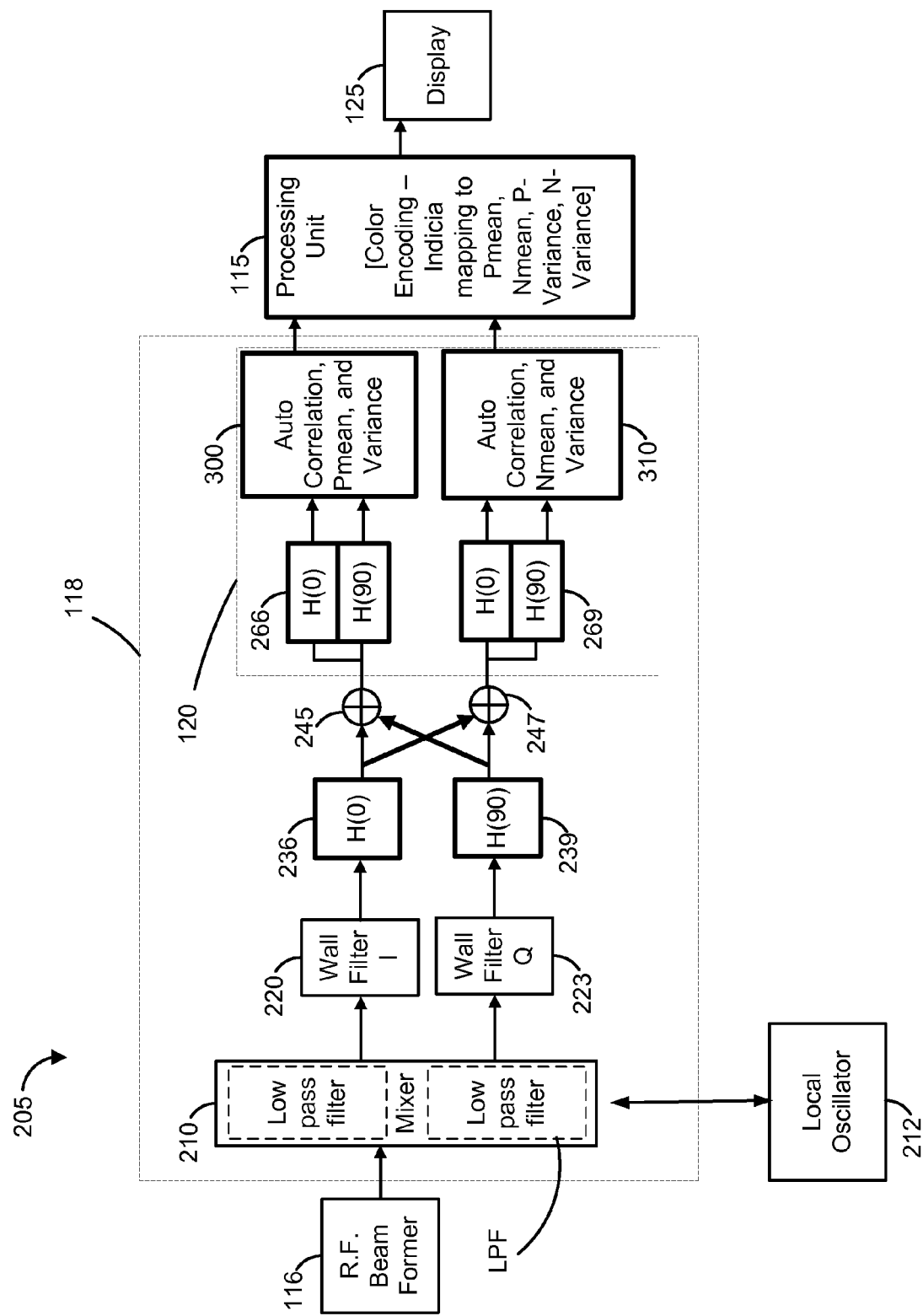
FIG. 3 is a block diagram of an ultrasound system configured to implement or include one or more color flow processing systems or methods in accordance with an embodiment of the invention.

FIG. 3 shows an ultrasound subsystem 205 suitable for use with the ultrasound system 10 of FIG. 1 and other ultrasound systems. The subsystem 205 includes additional components and additional details including the post-processing Hilbert transform (or other analytic signal generating transforms) and auto correlation system 120. In the ultrasound system 10 and subsystem 205 of FIGS. 1 and 3, respectively, the received signal from a sample such as sample 20 is transmitted to the front end beam-former 116. The signals received from the sample energize a transducer in probe 101 and generate R.F. signals that are processed using quadrature sampling at the front end beam-former 116 and mixer 210 to form I/Q signal pairs. The R.F. signals are generated in response to the echo signals impinging on each element of the transducer array in the probe. In a quadrature demodulation system, a mixer 210 is used to shift the RF frequency down to the baseband in order to extract the Doppler phase shift. In this way, the mixer 210 forms the I/Q baseband signal. The 'I' stands for In-Phase, and the 'Q' stands for Quadrature-Phase. The I baseband signal and Q baseband signal have a 90 degree phase difference relative to each other and constitute a signal pair along each color acquisition line. As shown, in the subsystem 205 of FIG. 3, the mixer 210 can include one or more low pass filters (LPF). The mixer can also be in electrical communication with a local oscillator 212.

In color flow ultrasound data acquisition, there are many color sample volumes (such as for example about 1 to about 200) in each color line. Each line includes a plurality of color signals resulting from multiple interrogations of a sample of interest, such as sample 20 of FIG. 1, to form an ensemble packet. As shown, in FIG. 3, following the output port of the mixer 210 output, after the I/Q baseband signal pair is formed, a pair of wall motion filters 220 and 223 are used to remove certain unwanted signals such as stationary vessel features or vessel wall motion data in the signal pair. Specifically, in one embodiment the signals associated with stationary tissue or vessel wall motion are removed from the I/Q baseband signal pair using such filters 220, 223.

Autocorrelation Embodiments for Signal Processing and Flow and Variance Calculations Once the stationary and vessel wall motion related features are removed from the signals, then the blood velocity can be determined using a suitable process such as auto-correlation algorithms or processes as shown in the first and second auto correlation processing stages or subsystems 300 and 310 within system 120 of FIG. 3. For example, the phase angle is calculated by using equation arctangent (Q/I), and the angular velocity is the difference of the phase angle in the ensemble packet.

For input data $X_1, \ldots, X_n, X_{n+1}, \ldots, X_N$, $6 \leq N \leq 12$ the auto-correlation function of the data set is:

$$R_{xx}(-1) = \sum_{1}^{N} X_n \cdot X_{n+1}^*$$

With $(I_n, Q_n)$ data set at a specific sample volume, $$R_{xx}(-1) = \sum_{1}^{N} (I_n + jQ_n) \cdot (I_{n+1} - jQ_{n+1})$$
$$= \text{Re} + j\text{Im}$$

Where $$\text{Re} = \sum_{1}^{N} (I_n \cdot I_{n+1} + Q_n \cdot Q_{n+1}), \text{Im} = \sum_{1}^{N} (I_{n+1} \cdot Q_n - I_n \cdot Q_{n+1}).$$

Re is the vector dot product term, and Im is the vector cross product term. From the above equation, we have $$\Delta\Phi = -\tan^{-1}\left(\frac{\text{Im}}{\text{Re}}\right)$$

The variance of the flow velocity is derived from $$\mu = \sigma^2 = \frac{2}{T^2}\left(1 - \frac{|R_{xx}(T)|}{R_{xx}(0)}\right) = \frac{2}{T^2}\left(1 - \frac{(Re^2 + Im^2)^{1/2}}{R_{xx}(0)}\right)$$

Where $R_{xx}(0) = \Sigma X_n \cdot X^*_n = \Sigma(I_n^2 + Q_n^2)$.

Color flow processing is based on the Doppler principle. When the detected flow is moving toward the transducer, the mean velocity estimate yields a positive number as an output. This positive number is then used to identify the flow as part of the data set. For example, the positive number can be used by the processing unit or processor 115 and associated encoded or data processing software to associate the positive flow velocity with a color such as a red color or with other indicia such as flashing pixels or hatching. In contrast, when the detected flow is moving away from the transducer, the mean velocity estimate yields a negative number, and the system encodes it with a blue color or other indicia. In this way, positive and negative flow information can be identified and shown to the user such as via display 125.

The application of the Hilbert transforms 236, 239, summing of signals using summers 245, 247 and the transforms 266, 269 of FIG. 3 perform positive and negative flow separation in the subsystem 205 of FIG. 3 before using separate autocorrelation processes for the respective negative and positive signals. Prior to discussing other features relating to the foregoing transforms and summers of the subsystem 205 of FIG. 3, it is useful to consider some features relating to how color flow mapping and signal processing are handled for an embodiment of the invention.

In many cases, the processor also calculates the variance or turbulence of the flow velocity, and uses additional indicia such as a green color to the original color map. In one embodiment, the first and second auto correlation processing stages or subsystems 300 and 310 can be implemented in hardware or software, including as instructions executed by the processing unit 115. As a result, with indicia for the positive flow, the negative flow, and variance or turbulence, various representational schemes can be used to display the data to a user of the system. For example, the positive flow, if encoded using a red color, can be shown with variance, encoded with a green color, to give a yellow color representative of positive flow and variance.

Similarly, if the negative flow is encoded with blue, when the negative flow and the variance signals overlap, the resulting indicia can be shown as a cyan color. In one embodiment, the various indicia and the rules for assigning them are stored in software and executed using components in system 120 or processing unit 115 and are customizable based on a user's preference in terms of how a first flow velocity in a first flow direction, a second flow velocity in a second flow direction, and variance or turbulence are displayed together relative to the ultrasound scan data such as an image of an anatomical structure.

As part of the processes of identifying and encoding a flow direction, the processor-based system is configured based on the constraint that the flow signal is only positive or negative within the same vessel. This is generally true because the blood inside a vessel is either flowing towards or away from the heart and does not flow in both directions in one vessel. There are circumstances where signals can cause unwanted effects such as blood appearing to be moving in two directions in a vessel or other unwanted visual artifacts.

Figure 4:
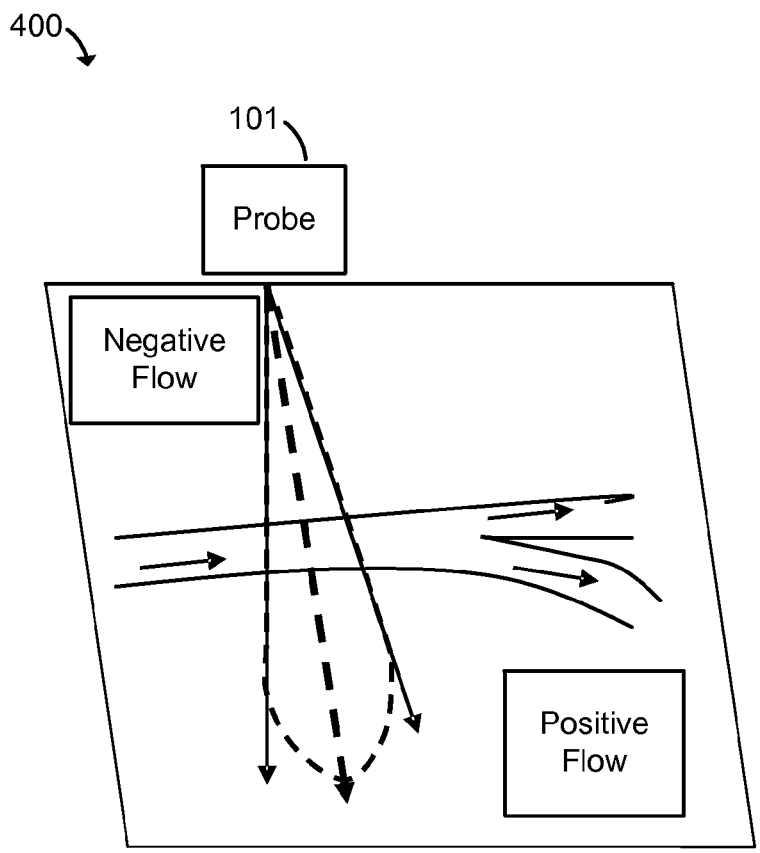
FIG. 4 is a schematic diagram of a color flow image of a blood vessel generated with a transversal Doppler ultrasound artifact when the Doppler angle is close to 90 degrees.

For example, in the case when the Doppler angle is close to 90 degrees as shown in FIG. 4, there will be transversal flow due to the side lobe or broadening of the beam. When the Doppler angle approaches 90 degrees and the beam width is broadened, there will be some energy above 90 degrees and some below. This spread of energy relative to the 90 degree phase level can result in values associated with both positive and negative flow being present in the receiving echo even though the blood flow is actually moving in one direction. When the received echo from the sample has both positive and negative flow information simultaneously present, the resulting display is factually inaccurate, and steps need to be taken to compensate for this scenario.

In the case where positive and negative flow information is simultaneously present, the flow with associated with a higher energy signal (greater amplitude in the signal) dominates the mean velocity detection, and the mean value can be biased based on the higher energy/amplitude associated with one of the two flow directions. If the Doppler angle at the center of the beam is exactly 90 degree, and the positive and negative flow is symmetrical due to the side-lobe. As a result of this symmetry, the mean velocity will be zero. An imaging artifact will then result such that no blood appears to shown in the vessel at all. Thus, users are trained to avoid using 90 degree Doppler angle when taking the flow image if possible. The reason for this problem is that legacy methods do not separate the flow direction before calculating the mean and variance using an auto-correlation algorithm. The Hilbert transforms 236, 239, summing of signals using summers 245, 247 and the Hilbert transforms 266, 269 of FIG. 3 perform positive and negative flow separation. These features allow for improved flow direction resolution and display in color mode.

Figure 5:
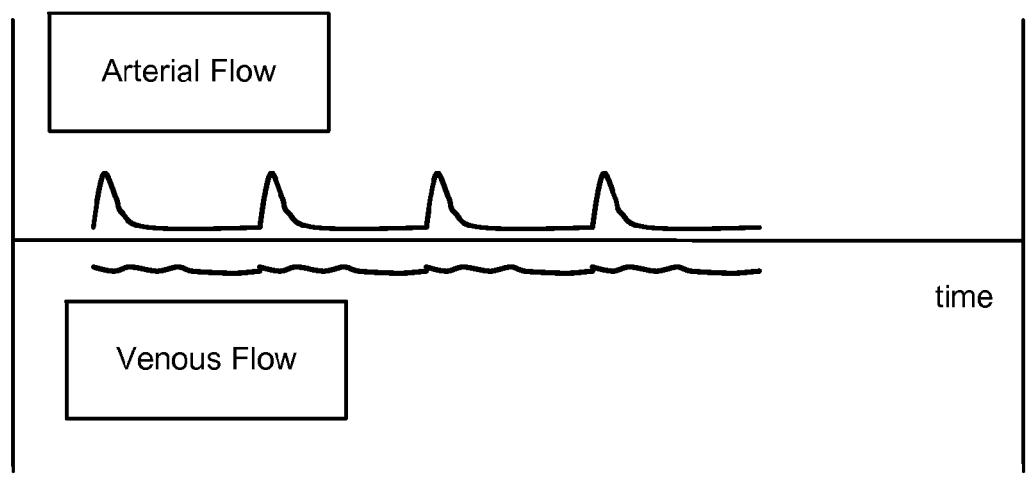
FIG. 5 is a schematic diagram of arterial and venous flow in a sample of interest such as in a kidney suitable for evaluation using a conventional spectral Doppler FFT method that illustrates flow direction ambiguity problem that is addressed by an embodiment of the invention.

FIG. 5 is a schematic diagram of arterial and venous flow in a sample of interest suitable for evaluation using a spectral Doppler FFT method according to an embodiment of the invention. FIG. 5 is the spectrum in PW Doppler mode with FFT method which can be used for the positive and negative mean estimate. In FIG. 5, the vertical axis is frequency; up for positive and down for negative, with zero hertz at baseline. The horizontal axis is time, and the brightness is for intensity, which is amplitude related.] Given the problems described above, one solution to overcome the flow direction-related problems and ambiguities are to use a fast Fourier transform (FFT) method to perform the color flow mapping and process the signals using various transforms and autocorrelation methods. By separating the flow signals prior to performing autocorrelation, the color encoding performed by the processing unit with regard to Pmean, Nmean, P-Variance, N-Variance is improved. This follows, in part, from the separate treatment of positive and negative flow data such as through the application of the transforms described herein.

For example, according to one embodiment, the FFT, as shown in FIG. 5 with complex I/Q data input, yields both positive and negative flow information in the Doppler spectrum. The arterial flow shown above the x-axis has a positive flow while the venous flow below the x-axis has a negative flow. In part, one embodiment of the invention relates to the application of a Doppler spectrum FFT method in color flow mode. The processor 115 can calculate the positive mean flow and negative mean flow separately using the full FFT spectrum as shown in FIG. 5. The processor can also calculate the mean and variance out of the spectrum for arterial flow above the baseline (x-axis_for the positive flow, and also do the same thing on the spectrum for venous flow below the baseline for the negative flow. These calculations can be performed using the processor and a set of scanned ultrasound data using the following equations in order to yield the Doppler shift frequency:

$$\bar{\omega}_+ = \int_0^\infty wP(w)dw / \int_0^\infty P(w)dw \text{ For positive flow mean}$$

$$\bar{\omega}_- = \int_{-\infty}^0 wP(w)dw / \int_{-\infty}^0 P(w)dw \text{ For negative flow mean}$$

P(w) is the power spectrum and ω is the angular velocity, which is the Doppler shifting frequency.

Another problem that can result from using FFT for the color flow processing relates to processing delays. Specifically, the FFT method will slow down the frame rate considerably (more than 10 times) on the multiple sample volumes because the size of the color ensemble packet needs to be increased from the typical number of 6-12 bursts or pulses from the imaging probe to at least 16-64 bursts or pulses in order to have the necessary velocity resolution. The reason is that the frequency resolution in FFT is determined based on the PRF (Pulse Interrogate Repetition Frequency) divided by the number of FFT points. Each pulse from the probe corresponds to one of the FFT points. For example, with a PRF of 16 KHz and an ensemble of 8 FFT points, the frequency resolution is 2 KHz (16 KHz/8). Unfortunately, this frequency resolution is too coarse for detecting a flow velocity. Specifically, if this frequency resolution is used with the FFT method, the processor being used for the FFT calculations will be subjected to a high processing load that will result in unreasonably long processing delays and slow down the frame rate. For these reasons, it is desirable to use autocorrelation based approaches for mean flow and variance calculations.

As a result, according to one embodiment of the invention, the ensemble size is adjusted to increase the granularity of the frequency resolution. For example, if the ensemble size of points for FFT is increased to 64 for example, the (64)(1/PRF) yields the time to collect a complete packet of data for FFT. As a result, if the PRF is 2 KHz and the FFT uses 64 points, then the total time period for acquiring 64 points of data is 0.5 milliseconds*64=32 milliseconds (ms). The blood flow occurring within a 32 ms time period cannot assume to be stationary, especially in the systolic cardiac phase. The blood flow velocity may change significantly during the 32 ms time span, especially when the patient has stenosis in the vessel. Changes in flow velocity during data acquisition can cause a spectral broadening artifact and bias the mean velocity calculation. One embodiment of the invention relates to selecting the time domain for signal processing purposes to reduce the data acquisition period such that it ranges from about 32 ms to about 2 ms to reduce or prevent the occurrence of spectral broadening artifacts.

In order to reduce the data acquisition period, according to one embodiment of the invention, it is useful to use a transform, such as a Hilbert transform to perform signal processing in the time domain and reduce the data acquisition period used in the processing. The system of FIG. 3 is configured to mitigate such unwanted artifacts resulting from long data acquisition periods, such as for example data acquisition periods greater than 32 ms.

Returning to subsystem 205 of FIG. 3, an in-phase wall filter 220 transmits an in-phase signal. The in-phase signal has no phase shift, which is equivalent to zero degree phase shift. In contrast, the quadrature phase wall filter 223 transmits a quadrature phase signal. The quadrature phase signal has a 90 degree phase shift. A first Hilbert transform 236 is applied to or otherwise operates upon the in-phase signal from wall filter 220 to generate a Hilbert transformed in-phase signal. In parallel with the processing of the in-phase signal, a first Hilbert transform 239 is applied to or otherwise operates upon the Quadrature phase signal from wall filter 223 to generate a Hilbert transformed Quadrature phase signal.

Upon the application of each of these first Hilbert transforms on the respective vessel wall motion filtered in-phase and Quadrature phase signals, any real signal that has no energy (zero amplitude) at zero Hz is generated as an output signal along with the imaginary part of the signal. As a result, the application of a Hilbert transform to a suitable signal can yield a complex analytic signal at the 236 and 239 outputs. According to some implementations of the invention, a Hilbert transform is used multiple times in different ways. The application of the Hilbert transforms 236, 239 in FIG. 3 are each configured to operate on a signal from the filter 220, 223. They are in electrical communication with and to perform all pass filtering based on phase angle.

Figure 7:
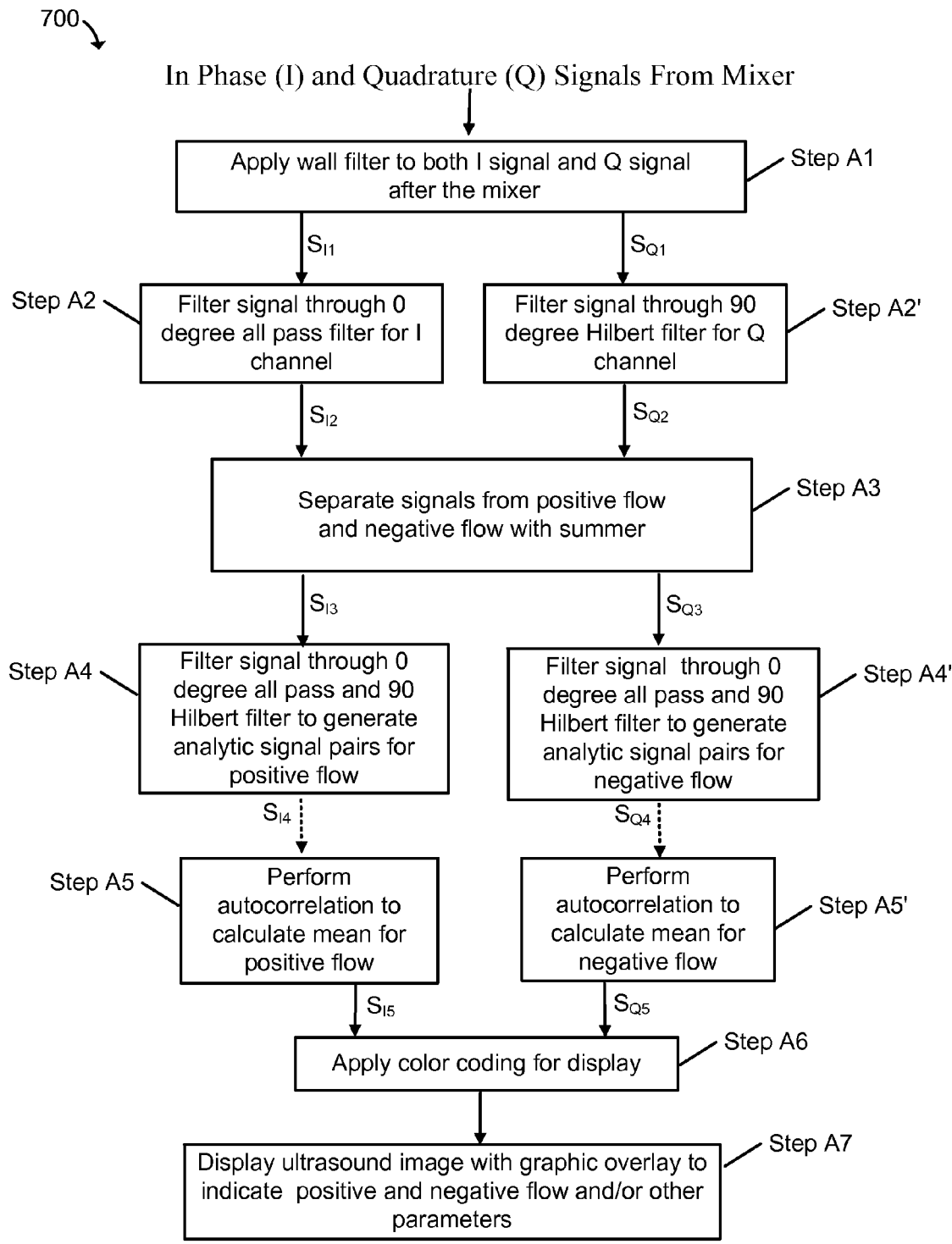
FIG. 7 is a process flow showing various signal processing steps or stages according to an embodiment of the invention.

Additional details relating to these signals and their processing is described herein, including with regard to the spectrum representations of FIG. 6 and the exemplary method steps of FIG. 7. The Hilbert transforms 236, 239 can be implemented using one or more filters such as an all pass filter configured for phase delay rather than amplitude attenuation. Hilbert transforms 236, 239 can also be implemented with a finite impulse response (FIR) filter or an infinite impulse response (IIR) filter. In one embodiment, digital filters are used.

In FIG. 3, in communication with the mixer 210 output as noted above, the wall filters 220, 223, which can be high pass filters, are used to remove the direct current (D.C.) stationary signal and signals associated with very slow vessel wall movement. In this way, the I/Q baseband signals are processed to retain flow velocity information while removing stationary and vessel wall movement contributions. In addition, this filtering step is performed to provide a signal that will satisfy the condition of Hilbert transform at the next signal processing stage in which the zero degree phase shift Hilbert transform 236 and the 90 degree phase shift Hilbert transform 239 operate on the wall filtered signals.

As shown in FIG. 3, the Quadrature phase Hilbert transform (90 degree shifter) 239 and the in-phase Hilbert transform 236 are in electrical or otherwise in communication with a first summer 245 and a second summer 247. In one embodiment, the Hilbert transform as a function of the phase shift S is of the form H(s) such that for a zero degree phase shift the transform is H(0) and for a 90 degree phase shift the transform can be expressed as H(90). The summers 245 and 247 are used to separate the positive flow and negative flow signals from the I/Q signals entering the summers 245, 247.

Following signal processing using the summers 245, 247, additional Hilbert transforms are applied to the positive flow signal and negative flow signal transmitted from summers 245 and 247. The additional Hilbert transforms 266 and 269 are used to convert or transform such real signals into an analytic format. This format is suitable for the autocorrelation processors 300 and 310 in the next processing stage, and can be used to calculate positive and negative mean separately. The autocorrelation method solves the problem of spectral broadening artifacts by reducing the data collection period and/or the number of data points needed generate an analysis relating to flow.

In FIG. 3, after the summer 245, transform 266 includes a Hilbert transform pair designated as H(0) and H(90) with phase angles 0 and 90 degrees, respectively. Transform 269 also includes a Hilbert transform pair designated as H(0) and H(90) with phase angles 0 and 90 degrees, respectively. These respective transform pairs are used to generate the analytical signals using the real signal for each of positive and negative flow on the 245 and 247 outputs. The analytical format is desirable prior to using the autocorrelation processes on such analytic signals to obtain mean flow estimates.

In a FFT method, the signals are converted into frequency domain spectrum, and the mean is calculated using the spectrum. In contrast, in the time domain autocorrelation method of the invention, the signals are converted into analytic format with a Hilbert transform or other analytic signal transform, and then the mean flow velocity in a direction is obtained using an autocorrelation function as described herein. Autocorrelation addresses phase shift directly and thus does not require long data set as required by the FFT method.

By using a time domain set of signals, such as can be generated using Hilbert transforms 266 and 269, the signal processing still remains in the time domain with a short or size-reduced ensemble packet. Therefore, the computation load is lower when compared with the FFT method discussed above that uses a frequency resolution of 2 KHz in the example given. In addition, after processing using autocorrelation processes 300, 310 values for Pmean, Nmean, P-Variance, N-Variance) are generated which can then be mapped to indicia using the processing unit. In one embodiment, the autocorrelation processes 300, 310 are implemented using a digital signal processing integrated circuit, a FPGA circuit, or other electronic processor device or circuit.

In one embodiment, other orders of processing using the Hilbert transform can be used. Thus, Hilbert transforms used to generate analytic signals can be applied first and then Hilbert transforms can be applied later to separate the flow data. In one embodiment, the mixer used is a complex signal mixer.

Certain features of an embodiment of the invention can summarized and explained by comparing various signal data from a frequency spectrum point of view. FIG. 6 shows various signals that are generated and processed according to various signal processing stages and methods of the invention such as pursuant to the method of FIG. 7 or as implemented using system 205 or components thereof. The signals shown in FIG. 6 are depicted in a frequency domain or space. As shown in FIG. 6, in-phase is for positive flow, and Q phase is for negative flow.

FIG. 6 shows various frequency spectrums 500 in which frequency values corresponding to values along the x-axis or horizontal axis. In contrast, the vertical or y-axis is used to display intensity values or amplitude values for a particular frequency f such as by the intensity function H(f). The carrier frequency for the ultrasound signal is represented as fc in FIG. 6. Typically, a demodulation system is used to remove this frequency prior to signal processing. The negative carrier frequency −fc is shown by the left dotted vertical line. In contrast, the positive carrier frequency fc is shown by the right dotted vertical line. The various signals are represented as arrows corresponding to their frequency and flow direction or other parameter of interest such as variance or positive or negative mean flow values.

For example, the arrows identified with a f2 or B in FIG. 6 can be shown on a display using a blue color (or other suitable first color or indicia) and correspond to a blood flow signal or value that indicates flow away from the transducer. The arrows identified with an f1 or R in FIG. 6 can be shown on a display using a red color (or other suitable second color or indicia) and correspond to a blood flow signal or value that indicates flow toward the transducer.

Starting at the top of FIG. 6, the first signals shown in the frequency space representation of FIG. 6 are radiofrequency (RF) signals. The RF signals shown in the first horizontal spectrum plot of FIG. 6 are the input spectrum. The RF signals include a signal 505 having a positive Doppler frequency f1 which is set above the carrier frequency fc and associated with a red (R) color for purposes of this explanation or subsequent use in a color flow mapping and to indicate the direction of flow. In addition, the RF signals include a signal 507 having a negative Doppler frequency f2 which is set below the carrier frequency fc and associated with a blue (B) color corresponding to an opposite flow direction. In one embodiment, as a convention red (R) is used for positive flow f1 and blue (B) is used for negative flow f2 as a convention.

In one embodiment, signals 505 and 507 are generated as pure sine waves such that the spectrum for each signal is a line positioned at its frequency. Since the RF signals are real valued signals, mirrored signals can result. RF signals 505, 507 having frequencies f1 and f2 are disposed in the positive side of the spectrum while corresponding mirror signals 505m and 507m (shown with dotted lines) are positioned on the negative side of the frequency axis on either side of a negative −fc axis. Signals 505m and 507m are mirrored versions of signals 505 and 507 respectively. The inclusion of "m" after the designator of another signal indicates that such a signal is a mirror.

Similarly, for the spectrum B of FIG. 6, the in-phase signals at baseband (IBB) 515 and 517 and their mirror signals 515m and 517m are shown. The spectrum C of FIG. 6 shows the Quadrature phase signals at baseband (QBB) 520 and 525 and their mirrors 520m and 525m. The mirror signals 520m and 525m for the QBB spectrum are inverted with a negative amplitude. The negative amplitude is a representation for mathematical operation purposes such for the operation of Hilbert transform, autocorrelation functions, and other processes and operations.

With regard to the in-phase channel of spectrum B, the radiofrequency signal is frequency shifted down to the baseband, the 0 Hz axis, through a mixer 210 used in the ultrasound system 205. In one embodiment, the mixer 210 can include or be in electric communication with one or more low pass filters (LPF). The f1 signal 505 in the RF spectrum moves to the position of signal 515 in the IBB spectrum and its mirror 505m moves to the position of signal 515m in the IBB spectrum. The f2 signal 507 moves to the position of signal 517 in the IBB spectrum and its mirror 507m moves to the position of signal 517m. The Doppler frequency signals transition to new frequencies in the IBB spectrum because the f1 signal and f2 signal in the radiofrequency spectrum are at both upper and lower sidebands around the fc carrier.

Referring to FIG. 3, the IBB signals are the output signals from in-phase wall filter 220. Similarly, the QBB signals are the output signals from quadrature phase wall filter 223. The quadrature phase channel baseband signals generated after the first Hilbert transform are identified as QBBH and are shown on spectrum D of FIG. 6. The QBBH signals include signal 530 and 535 and their mirrors 530m and 535m as shown on spectrum D of FIG. 6. The QBBH signals are output from signal processing stage 239 in which a Hilbert transform is applied with a 90 degree shift to the QBB signals.

As part of the signal processing of summers 245 and 247, the summing together of the QBBH signals and the IBB signals is performed as shown in the spectrum E of FIG. 6. Signals 517 and 517m from the IBB spectrum having upward directed arrows cancel signals 535 and 535m from the QBBH spectrum with the downward directed arrows as shown in the IBB+QBBH spectrum also referred to as spectrum E in FIG. 6. In spectrum E, as shown signal 540 with Doppler frequency f1 and its mirror 540m remain while the f2 signal in the lower sideband is removed.

A difference operation can be performed to show the f2 Doppler signal remaining with the f1 signal being removed in the F spectrum. Specifically, a difference calculation, which can also be performed using summers 245 and 247, is performed in which the QBBH signals are subtracted from the IBB signals as shown in spectrum F of FIG. 6. This results in signal 550 with Doppler frequency f2 remaining as the baseband f2 flow with its mirror signal 550m with the f1 signal and its mirror removed. Accordingly, as a result of the Hilbert transform to generate the QBBH signals, the addition operation of spectrum E, and the difference operation of spectrum F provide a process for the positive flow and negative flow to be separated as evidenced by the real signal 540 with Doppler frequency f1 and real signal 550 with Doppler frequency f2.

Signals 550 and 540 (and their mirrors, in one embodiment are processed using the second Hilbert transforms 266, 269 to generate complex signals 560 and 570 corresponding to different flow directions in spectrum G and H. Signal 560 corresponds to the analytic positive flow signal and signal 570 corresponds to the analytic negative flow signal. The transforms 266, 269 that results in signals 560, 570 processes the signals into a complex (or analytic) format suitable for use with autocorrelation methods in signal processing stages 300, 310 such that mean value calculations and variance can be determined with regard to the transforms of signals 560 and 570. After the performance of the autocorrelation method in signal processing stages 300, 310, the final result is the positive mean (also referred to as PMean) and the negative mean (also referred to as NMean). The resultant PMean signal 580 and the NMean signal 585 are shown on the spectrum plots I and J of FIG. 6 at the bottom of the figure. The variance can also be calculated using an autocorrelation function.

FIG. 7 is a flow diagram of a signal processing method 700 according to an illustrative embodiment of the invention. In one embodiment, the method relates to various signal and data processing steps relative to ultrasound data obtained with respect to a patient. In one embodiment, In-phase (I) signals and Quadrature (Q) signals originating from a mixer are the input signals. These are typically I/Q signal pairs. The mixer, for example, may be the mixer 210 described with regard to FIG. 3, although other mixers, beam formers, and other sources of I and Q signals can be used with the steps of the method 700.

In one embodiment, the method includes 700 applying a wall filter to both the I signal and the Q signal output from a mixer or other signal processing device (Step A1). Various signal processing steps can be performed as part of the method 700. The various steps of the method can be performed by a processor or other circuits or devices as described herein, for example, such as those depicted in FIGS. 1 and 3. As a convenience, various signals generated as result of the processing of the In-phase signal are designated as SI1, SI2, SI3, SI4, and SI5. Similarly, as a convenience, various signals generated as result of the processing of the Quadrature signals are designated as SQ1, SQ2, SQ3, SQ4, and SQ5. Thus, for example, the signals resulting from the wall filter application of Step A1 are signals SI1 and SQ1.

In turn, signal SI1 can be filtered through a 0 degree all pass filter for the I channel as shown in Step A2. The output of the zero degree all pass filtering of signal SI1 is output signal SI2. In contrast, signal SQ1 is filtered through a 90 degree Hilbert filter through the Q channel as shown in Step A2'. The output of the 90 degree Hilbert filtering of signal SQ1 is output signal SQ2. The Hilbert filtering performed in Step A2 and A2' can correspond to the transforms 236 and 239 being applied to a signal in FIG. 3.

Next, these two signals are separated based upon positive flow and negative flow characteristics using one or more summers as shown in Step A3. Two summers can be used such as summers 245 and 247. The signals that result from processing using the summer are signals SI3 and SQ3. Additional processing based upon the positive and negative flow associated with the respective signals is then performed using Steps A4 and A4'.

With respect to step A3, signal SI3 is filtered through a 0 degree all pass filter and a 90 degree Hilbert filter to generate analytic signal pairs for positive flow in the form of one or more signals SI4. In contrast, with respect to step A3, signal SQ3 is filtered through a 0 degree all pass filter and a 90 degree Hilbert filter to generate analytic signal pairs for negative flow in the form of one or more signals SQ4. In one embodiment, at this point in the signal processing a total of four Hilbert transforms or Hilbert filters (236, 239, 266, and 269) have been applied, twice for the In-phase and Quadrature signals, and twice for the positive and negative flow signals.

Following the application of the Hilbert filtering of Steps A4 and A4', autocorrelation steps A5 and A5' are performed relative to each of the signals, SI4 and SQ4, respectively. Specifically, a processor performs autocorrelation with respect the SI4 signal to calculate mean for positive flow SI5. Similarly, with regard to the negative flow, a processor performs autocorrelation with respect the SQ4 signal to calculate mean for negative flow SQ5. Step A6 includes applying color coding for ultrasound display based on the mean positive flow and the mean negative flow. Further Step A7 includes displaying an ultrasound image with a graphic overlay corresponding to positive and negative flow information. Variance values can also be calculated for the positive and negative flows using the processing unit or autocorrelation methods.

In step A6, the flow data is used to encode image data such that a user can view a color map based. The color map is arrived at based on signal processing that includes a flow signal separation step and two separated autocorrelation processes. The color map can be displayed with various legends or codes to map indicia to flow directions and variance values in Step A7.

The present disclosure discusses embodiments in the context of ultrasound imaging systems, however, these embodiments are not intended to be limiting and those skilled in the art will appreciate that the present disclosure can also be applied to other imaging systems.

The aspects, embodiments, features, and examples of the present disclosure are to be considered illustrative in all respects and are not intended to limit the invention, the scope of which is defined only by the claims. Other embodiments, modifications, and usages will be apparent to those skilled in the art without departing from the spirit and scope of the present disclosure.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the present disclosure; each section can apply to any aspect, embodiment, or feature of the present disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a system, a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions or operations is immaterial so long as the present teachings remain operable. Moreover, two or more steps or actions or operations may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The present disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In one embodiment of the present invention, some or all of the processing of the data used to generate a control signal or initiate a user interface command is implemented as a set of computer program instructions that is converted into a computer executable form, stored as such in a computer readable medium, and executed by a microprocessor under the control of an operating system. In one embodiment, output control signals from a controller are transformed into processor understandable instructions suitable for color flow mapping, signal separation, flow calculation, color flow mapping, variance calculation, autocorrelating separated flows signals, analytic signal transforms, phase-based filters, Hilbert transforms, and other features and embodiments as described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. For example, a computer program product may reside on a computer readable storage medium having a plurality of instructions stored thereon, which, when executed by a processor, cause the processor to perform operations discussed herein.

The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed over a network.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as ultrasound modes, color modes, ultrasound mammography data, ultrasound infant or prenatal data, ultrasound cardiac data, icons, touch screen primitives, and other information of interest.

Computers and computer systems described herein may include an operatively associated machine-readable medium such as computer-readable media such as memory for storing software applications used in obtaining, processing, storing and/or communicating data. It can be appreciated that such memory can be internal, external, remote or local with respect to its operatively associated computer or computer system.

The term "machine-readable medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media.

It is to be understood that the figures and descriptions of the invention have been simplified to illustrate elements that are relevant for a clear understanding of the present disclosure, while eliminating, for purposes of clarity, other elements. Those of ordinary skill in the art will recognize, however, that these and other elements may be desirable. However, because such elements are well known in the art, and because they do not facilitate a better understanding of the present disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure.

The examples presented herein are intended to illustrate potential and specific implementations of the present disclosure. It can be appreciated that the examples are intended primarily for purposes of illustration of the present disclosure for those skilled in the art. There may be variations to these diagrams or the operations described herein without departing from the spirit of the present disclosure. For instance, in certain cases, method steps or operations may be performed or executed in differing order, or operations may be added, deleted or modified.

Furthermore, whereas particular embodiments of the present disclosure have been described herein for the purpose of illustrating the present disclosure and not for the purpose of limiting the same, it will be appreciated by those of ordinary skill in the art that numerous variations of the details, materials and arrangement of elements, steps, structures, and/or parts may be made within the principle and scope of the present disclosure without departing from the invention as described in the claims.

What is claimed is:

1. A method of ultrasound color flow mapping comprising:
   separating a positive flow signal and a negative flow signal from ultrasound data by transforming the ultrasound data using a first pair of Hilbert transforms and summing output signals from the pair of Hilbert transforms using one or more summers to generate a separated positive flow signal and a separated negative flow signal;
   converting the separated positive flow signal and the separated negative flow signal into a positive flow analytic signal and a negative flow analytic signal using a second pair of Hilbert transforms;
   autocorrelating the positive flow analytic signal to obtain a mean positive flow velocity;
   autocorrelating the negative flow analytic signal to obtain a mean negative flow velocity; and
   performing color flow mapping using the mean positive flow velocity and the mean negative flow velocity.

2. The method of claim 1 further comprising determining a flow velocity variance associated with the mean positive flow velocity or the mean negative flow velocity.

3. The method of claim 2 wherein performing color flow mapping further comprises using the flow velocity variance.

4. The method of claim 1 further comprising collecting the ultrasound data using a probe.

5. The method of claim 4 further comprising selecting a data acquisition period during which the ultrasound data is collected by the probe that ranges from about 2 milliseconds to about 32 milliseconds.

6. The method of claim 5 further comprising the step of selecting the data acquisition period to reduce occurrence of a spectral broadening artifact.

7. The method of claim 4 further comprising selecting a pulse repetition frequency in the range of from about 1 KHz to about 50 KHz for the probe.

8. The method of claim 1 further comprising performing the autocorrelation steps using the positive flow analytic signal and the negative flow analytic signal in the time domain.

9. The method of claim 1 further comprising
applying a first indicia to ultrasound image data corresponding to the mean positive flow; and
applying a second indicia to ultrasound image data corresponding to the mean negative flow.

10. The method of claim 9 further comprising displaying the first indicia and the second indicia overlaid on a B-mode ultrasound image.

11. The method of claim 9 further comprising assigning a first color code for the mean positive flow, assigning a second color code for the mean negative flow, and assigning a third color code for the flow with both positive and negative flow.

12. The method of claim 1 wherein the ultrasound data comprises one or more RF signals and further comprising
wall filtering the one or more RF signals to remove vessel wall motion; and
frequency shifting the positive flow analytic signal and the negative flow analytic signal using a mixer.

13. The method of claim 1 wherein a phase angle for one Hilbert transform of the first pair is set at about 0 degrees and a phase angle for the other Hilbert transform of the first pair is set at about 90 degrees.

* * * * *